US012761207B2

(12) United States Patent
Hall et al.

(10) Patent No.: US 12,761,207 B2
(45) Date of Patent: Oct. 13, 2026

(54) CALIBRATION AND PROFILING OF A NANOPORE ARRAY DEVICE

(71) Applicant: Oxford Nanopore Technologies PLC, Oxford (GB)

(72) Inventors: Graham Hall, Oxford (GB); Max Fletcher Wilson, Oxford (GB); Daniel Benjamin Trevor Ward, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 831 days.

(21) Appl. No.: 18/189,638

(22) Filed: Mar. 24, 2023

(65) Prior Publication Data

US 2023/0296582 A1 Sep. 21, 2023

(30) Foreign Application Priority Data

Mar. 21, 2022 (GB) ..................................... 2203944

(51) Int. Cl.
*G01N 33/487* (2006.01)

(52) U.S. Cl.
CPC .............................. *G01N 33/48721* (2013.01)

(58) Field of Classification Search
CPC ................................................ G01N 33/48721
See application file for complete search history.

(56) References Cited

U.S. PATENT DOCUMENTS

2020/0033292 A1 1/2020 Washizu
2020/0283844 A1* 9/2020 Huo ..................... C12Q 1/6869
2021/0018464 A1 1/2021 Ali et al.

FOREIGN PATENT DOCUMENTS

WO WO 2000/028312 A1 5/2000
WO WO 2005/124888 A1 12/2005
(Continued)

OTHER PUBLICATIONS

Ivanov et al., DNA tunneling detector embedded in a nanopore. Nano Lett. Jan. 12, 2011;11(1):279-85. doi: 10.1021/nl103873a. Epub Dec. 6, 2010.
Lieberman et al., Processive replication of single DNA molecules in a nanopore catalyzed by phi29 DNA polymerase. J Am Chem Soc. Dec. 22, 2010;132(50):17961-72. doi: 10.1021/ja1087612. Epub Dec. 1, 2010. Author Manuscript, 21 pages.
(Continued)

*Primary Examiner* — Aaron A Priest
(74) *Attorney, Agent, or Firm* — Wolf, Greenfield & Sacks, P.C.

(57) ABSTRACT

A method of calibrating a nanopore array device. The nanopore array device comprising: a common electrode, an array of sensing elements each comprising a sensing electrode and a nanopore channel, and an ionic solution in contact with the common electrode and the array of sensing electrodes, the ionic solution providing electrical communication between the common electrode and each of the array of sensing electrodes via the corresponding array of nanopore channels. The method comprises the steps of: applying a two or more test signals across the nanopore channels between the common electrode and array of sensing electrode measuring a corresponding current or voltage value associated with each sensing electrode for each test signal, determining an offset value for each sensing electrode from the measured current or voltage signals, and calculating a general offset value from the determined offset values, and applying a calibrated signal between the common electrode and sensing electrodes; wherein the calibrated signal is adjusted by the general offset value.

19 Claims, 3 Drawing Sheets

(56) References Cited

FOREIGN PATENT DOCUMENTS

| | | | |
|---|---|---|---|
| WO | WO 2009/077734 | A2 | 6/2009 |
| WO | WO 2010/055307 | A1 | 5/2010 |
| WO | WO 2010/086603 | A1 | 8/2010 |
| WO | WO 2010/122293 | A1 | 10/2010 |
| WO | WO 2011/067559 | A1 | 6/2011 |
| WO | WO 2012/005857 | A1 | 1/2012 |
| WO | WO 2012/033524 | A2 | 3/2012 |
| WO | WO 2012/107778 | A3 | 8/2012 |
| WO | WO 2012/164270 | A1 | 12/2012 |
| WO | WO 2013/153359 | A1 | 10/2013 |
| WO | WO 2014/064443 | A2 | 5/2014 |
| WO | WO 2014/064444 | A1 | 5/2014 |
| WO | WO 2015/140535 | A1 | 9/2015 |
| WO | WO 2015/150786 | A1 | 10/2015 |
| WO | WO 2016/034591 | A2 | 3/2016 |
| WO | WO 2016/181118 | A1 | 11/2016 |
| WO | WO 2018/100370 | A1 | 6/2018 |

OTHER PUBLICATIONS

Liu et al., Adding new chemistries to the genetic code. Annu Rev Biochem. 2010;79:413-44. doi: 10.1146/annurev.biochem.052308.105824.

Luan et al., Base-by-base ratcheting of single stranded DNA through a solid-state nanopore. Phys Rev Lett. Jun. 11, 2010;104(23):238103. doi: 10.1103/PhysRevLett.104.238103. Epub Jun. 10, 2010. Author Manuscript, 9 pages.

Soni et al., Synchronous optical and electrical detection of biomolecules traversing through solid-state nanopores. Rev Sci Instrum. Jan. 2010;81(1):014301. doi: 10.1063/1.3277116.

Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.

* cited by examiner

CALIBRATION AND PROFILING OF A NANOPORE ARRAY DEVICE

RELATED APPLICATION

This application claims the benefit under 35 U.S.C. § 119 (a)-(d) of Great Britain Application 2203944.0, filed Mar. 21, 2022, the entire content of which is incorporated by reference herein.

SUMMARY

The present invention relates to a method of calibrating and/or profiling a nanopore device. More particularly the invention relates to a method of calibrating and/or profiling a nanopore array device. Most particularly the invention relates to a method of calibrating and/or profiling a nanopore array device used for sensing molecular entities of an analyte.

The use of nanopores to sense interactions with molecular entities, for example polynucleotides is a powerful technique that has been subject to much recent development. Nanopore devices have been developed that comprise an array of sensing elements arranged to support respective nanopores, thereby increasing data collection by allowing plural nanopores to sense interactions in parallel, typically from the same sample.

Nanopore devices may typically employ an electrical signal across a nanopore channel to generate a measurement signal that is interpreted to sense and/or detect molecular entities as they interact with the nanopore. Typically an electrical signal is applied as a working voltage or current across the array of nanopore channels that will provide a meaningful measurement to be interpreted. This working electrical signal can be applied as a steady signal, or a variable signal. The measurement can include, for example, ionic current flow, electrical resistance, or voltage.

The working electrical signal for the array device is delivered to the system at a predetermined value or values. The fluctuation in the trace of the measurement can then be interpreted to determine the molecular entity present in the analyte. However, in practice the actual electrical signal applied across the nanopore channel can deviate from the intended working electrical signal. This deviation appears from variances in the system or device such as, for example, changes in the redox electrode mediator concentrations, ground variance across the array of electrodes, or fabrication errors in the device.

In addition, during use and/or over time the conditions of the nanopore device and system can change such that larger applied signal is required to achieve an acceptable measurement response. This can lead to a measurement trace that is less accurate and more susceptible to noise. This can also lead to the use of sensing elements that are defunct or impaired which may affect the overall output of the nanopore sensing device.

In a first embodiment the present invention relates to a method of calibrating a nanopore array device, the nanopore array device comprising: a common electrode, an array of sensing elements each comprising a sensing electrode and a nanopore channel, and an ionic solution in contact with the common electrode and the array of sensing electrodes, the ionic solution providing electrical communication between the common electrode and each of the array of sensing electrodes via the corresponding array of nanopore channels; the method comprising: applying a two or more test signals across the nanopore channels between the common electrode and array of sensing electrodes; measuring a corresponding current or voltage value associated with each sensing electrode for each test signal, determining an offset value for each sensing electrode from the measured current or voltage signals, and calculating a general offset value from the determined offset values, and applying a calibrated signal between the common electrode and sensing electrodes; wherein the calibrated signal is adjusted by the general offset value. The common electrode may be provided in a common chamber and the sensing electrodes are provided in respective wells. The ionic solution in the common chamber may be the same or of different to the ionic solution in the wells. The ionic solution in the common chamber may be of the same or of a different ionic strength or concentration to the ionic solution in the wells. As an alternative to providing a common electrode in a common chamber, the device may comprise more than one electrode. The device may have an array of such electrodes, herein referred to as counter electrodes provided in respective separate chambers, and an array of sensing electrodes. Each counter electrode would typically have an associated redox couple. Reference to a common electrode in the specification may be also be considered as a reference to two or more counter electrodes. A solution containing the analyte of interest will typically be added to the common chamber or separate chambers comprising the respective counter electrodes.

By employing the above calibration method, an offset value can be derived and used to calibrate or adjust the applied signal across the common electrode and the array of sensing electrodes. The calibrated electrical signal that is applied is the intended working electrical signal for the nanopore array device.

For instance, the nanopore device may require a working signal of, for example, a constant 180 mV signal applied across the common electrode and the array of sensing electrodes for a set period of time. During the calibration method of the present invention, the system is interrogated to reveal any chemical variations or system/device defects which might affect the working voltage applied to the system. The two or more test signals are applied to determine an offset value. The offset value can be described as a corrected baseline value that would generate a desired measurement signal (typically zero). This offset value is used to determine what calibrated electrical signal should be applied to the system to provide the desired working electrical signal.

In a particular embodiment using two test values, the first test signal could be the signal from a previously calibrated signal that has been used in the nanopore array device. In other words, the nanopore array device could be used such that a calibrated or uncalibrated signal is being used to generate a measurement signal, and a pseudo-test value could be taken in combination with another test value to determine the offset value for each sensing electrode. In other words, for this embodiment one specific test signal is required only for the calibration method, the other test value is one that is derived from a working signal and corresponding measurement from when the sensing electrode is being used as intended (for example, sensing molecular entities of an analyte).

Calibrating the nanopore array device using the method of the present invention provides the advantage of a more robust and reliable measurement signal when a calibrated signal is applied across the common electrode and the array of sensing electrodes. This also provides a more accurate measuring signal. The calibrated signal can also be adjusted by offset value to reduce noise in the measuring signal.

The calibrated signal may be a voltage, such that the test signals are also voltages and the offset value is a voltage, in this case the corresponding measurements associated with each test signal is a measurement of current. A current measurement provides information about the flow of ions through the nanopore channel and can be controlled effectively in a nanopore array device to provide consistent and reliable measurements for interpretation for the offset values.

The array of sensing electrodes may be divided into groups, such that a general offset value can be determined for each of the groups of sensing electrodes. A typical grouping for nanopore devices is based on multiplexing sensing electrodes (i.e. the electrical arrangement of the device). Such a configuration of an array of sensing elements with a plurality of detection channels and a switching arrangement is known from WO-2010/122293. Using the method of the present invention, the offset values can be used to profile the quality of each of the sensing elements. The sensing elements can instead be grouped based on the offset values generated during the calibration method of the present invention. In each example, a general offset value can then be applied to each group of sensing electrodes to ensure an improved calibrated working signal is applied to the system during use.

A global offset value may be determined across the array of sensing electrode. Since the common electrode is shared across the array of sensing elements, a single offset value (i.e. the global offset value) can be determined to generate the calibrated signal if two or more sensing elements are to be used at the same time. The global offset value may be determined using only a selection of the offset values from each sensing electrodes. In this example, outlying offset values may be discounted, and/or particular offset values may be weighted to provide an adjusted global offset value.

The method may include an additional step of carrying out a linear regression to determine the offset value. The linear regression is a method that can be employed to rapidly calculate to offset value using minimal computing power. The resulting plot from the linear regression gives an indication of the offset values required for each sensing electrode based on the intercept of the resulting plot at a point where the measurement signal should be zero. As mentioned above, chemical variations or system/device defects affect the required calibrated signal which would return a zero-value measurement signal. Additionally, due to the orders of magnitude being applied and measured, any float or variation in the ground voltage would impact the offset value.

The method may include estimating a gradient value from the linear regression. The gradient value can be used to determine another characteristic of the well. Generally the resistance or conductance can be derived from the gradient. The resistance or conductance for each sensing element can give an indication of its quality or performance. For example, the gradient value can be used for selecting sensing elements in which the nanopore channel has an acceptable number of nanopores inserted or formed. This selection can increase the utilisation of the nanopore array device in that only acceptable (or active) sensing elements are selected (or grouped as above). For some nanopore array devices, the formation of a nanopore channel is subject to random processes resulting in incomplete preparation of sensing elements of acceptable quality. However, in the present invention a single calibration method can be employed to determine accessible sensing elements and also a group or global offset value for the nanopore array device.

At least three test signals may be applied across the common electrode to give three or more corresponding current or voltage measurements associated with each test signal. Three or more test signals improve the confidence in the offset values and also the gradient values. They also provide a greater confidence in the linear regression detailed above.

The nanopore array device may further comprise a redox couple. The redox couple may be a soluble redox mediator in the ionic solution, and the sensing electrodes and common electrode may be selected from an inert metal such as gold, platinum or palladium. Well known redox couples suitable for use in the invention include ferricyanide (ferri) ($[Fe(CN)6]^{3-}$) and ferrocyanide (ferro) ($[Fe(CN)6]^{4-}$). The redox mediator is present as a local redox couple for each sensing electrode and is one way in which the conditions may vary across the array of sensing electrodes. The redox couple is present as a stable but shifting equilibrium between its two or more redox states. A sensing electrode with a local redox concentration that is not balanced would provide an offset value when tested. Therefore any variations in concentrations of the redox couple local to each sensing electrode before, during or after use of the nanopore array device would result in a need for calibration. The method of the present invention provides a way of calibrating each sensing electrode of the array, even after the nanopore array device has been used and there are unknown variations of redox couple local to each sensing electrode. An inert material means that the signal from the common electrode can be assumed to be stable and constant during the calibration. The redox couple may be an insoluble metal salt and the metal, such as silver/silver chloride. The metal may act as the current collector or for example be plated onto an inert metal. The device may comprise more than one type of redox couple. The redox couple associated with common electrode may for example be silver/silver chloride and the redox couple associated with the sensing electrodes may be ferri/ferrocyanide.

Depending upon the polarity of the signal between the common electrode and the sensing electrodes and the amount of charge passed, the ratio of the ionic strength or activity of the redox couple will change over time in accordance with the Nernst equation:

$$E = E^0 - \frac{RT}{zF}\ln Q$$

where Q=[activity of the reduced form]/[activity of the oxidised form].

During measurement for example of polynucleotides as analyte, negatively charged polynucleotides in the common chamber are translocated through the nanopore under a negative potential towards the sensing electrodes wherein the sensing electrodes are held at a negative potential relative to the common electrode. The reduced form of the redox couple at a sensing electrode, which may be ferricyanide will be oxidised over time to the oxidised form, ferrocyanide therefore affecting the ratio of Q and changing the redox potential. As can be seen from the above equation the electrode potential will shift more dramatically as the reduced form of the redox couple is depleted. Ultimately when all of the reduced form is oxidised, the potential at the electrode will no longer be fixed and will drift. This may be referred to as the electrochemical lifetime of the sensing electrode. To mitigate against depletion of one of the members of the redox couple, the potential at a sensing electrode may be reversed, typically during a period where measurement of the analyte does not take place, thereby generated the reduced form of the redox couple from the oxidised form.

Each sensing element in the array may comprise a well which houses a corresponding sensing electrode, and each nanopore channel may comprise a protein pore inserted in an amphiphilic membrane, such that the amphiphilic membrane extends across an opening of each of the wells. In an alternative arrangement, the nanopore channel may comprise a nanopore provided in a solid-state substrate. In both arrangements, the method may further comprise the step of measuring ion current through a nanopore under the application of the calibrated voltage. The ion current may be measured to determine the interaction of an analyte of interest with a nanopore. The analyte of interest may be a polynucleotide and the measured ion current is due to translocation of the polynucleotide through a nanopore.

The method may be performed after the calibrated signal has been used for one or more successive periods of time, such that new offset values, a new general offset value and a new calibrated signal may be calculated for each period of time. The period of time might be a predetermined interval or cycle, such as 90 minutes or longer. The period of time might also be set by the intended use of the nanopore array device. For example, the expected time it takes to pass the analyte of interest through the nanopore channel in the nanopore array. When a sensing electrode has an offset value falling outside of a threshold value it may be disconnected from the nanopore array device. That is to say that the sensing electrode is not included in any active sensing of an analyte since it might be ineffective or inactive. The offset value for a sensing electrode whose offset value is determined as being greater (i.e. falling outside of a threshold value) than the new threshold value may not used to calculate the general offset value. That is to say that the threshold can be set to exclude offset values that would impact on the functioning of the nanopore array device if the general offset value were influenced by them.

However, a sensing electrode may be reconnected after a further period of time where it is determined that the new offset value for said sensing electrode falls within a new threshold value. This is to take into account that the nanopore array device is a system in flux. The electrochemistry or the electrical needs of the system may vary, such that sensing electrode initially labelled as falling outside of a threshold amount may adjust over time and become effective. Likewise, the threshold value(s) may change over time and could depend on what is intended for analysis in the nanopore array device, or the required levels of confidence in the measurements by the user.

The test signals may be applied below a limit value relative to the calibrated signal. In use, the calibrated signal may be used to urge an analyte pass through the nanopore channel. In contrast, the test signals are designed to provide a measurement signal which is a baseline reading without analyte. Thus it is advantageous to provide a test signal below a limit value below a working signal which would cause analyte to flow through the nanopore channel. The limit might be an absolute number. For example, if the calibrated signal is 180 mV, then the test signals may be about 50 mV, 30 mV and 10 mV. Alternatively, the test signals may be expressed as a fraction of the intended calibrated signal. For example, half, a third or a quarter of the intended calibrated signal.

In a second embodiment the present invention relates to method of profiling a nanopore array device, the nanopore array device comprising: a common electrode, an array of sensing elements each comprising a sensing electrode and a nanopore channel, and an ionic solution in contact with the common electrode and the array of sensing electrodes, the ionic solution providing electrical communication between the common electrode and each of the array of sensing electrodes via the corresponding array of nanopore channels; the method comprising: applying a two or more test signals across the nanopore channels between the common electrode and array of sensing electrodes; measuring a corresponding current or voltage value associated with each sensing electrode for each test signal, determining an offset value for each sensing electrode from the measured current or voltage signals, and reviewing the offset values to generate a profile for each sensing element.

The test signals and corresponding measurements can be used to determine a profile for each sensing element to determine characteristics of the sensing electrodes. The characteristics might be based on binary profiles of good electrodes or bad electrodes (i.e. active and inactive sensing elements). Additionally or alternatively, the profiles might be based on particular suitability for sensing electrodes to analyse particular analytes and/or be used for particular periods of time.

In a particular example, the profiling might be used to classify sensing elements that require recharging or replenishing in order to make them active.

The method may further comprise the step of selecting sensing elements to receive a working signal based on their profile. It is advantageous to select sensing elements that show favourable qualities such as conductance and low offset values so that more accurate measurements might be taken when the nanopore array device is in use. Once the selection of sensing elements is made, a working signal is applied to the selected sensing elements to generate a measurement.

The nanopore array device may thus further comprise a redox mediator in the ionic solution, wherein the working signal is applied to adjust the redox chemistry of the mediator. As discussed above, the redox mediator is present as a local redox couple for each sensing electrode and is one way in which the conditions may vary across the array of sensing electrodes. The redox couple is present as a stable but shifting equilibrium between its two or more redox states. A sensing electrode with a local redox concentration that is not balanced would provide an offset value when tested. Therefore any variations in concentrations of the redox couple local to each sensing electrode before, during or after use of the nanopore array device would affect differently the ability of each of the sensing electrode to carry out a set of new measurements. Thus, the method of the present invention allows for accurate and real-time profiling of each of the sensing electrodes of the array. As above, an inert material means that the signal from the common electrode can be assumed to be stable and constant during the profiling.

As above, the method may be performed after the nanopore array device has been in use for one or more periods of time, such that new offset values are determined, and a new profile for each sensing element is provided for each period of time.

BRIEF DESCRIPTION OF THE DRAWINGS

To allow better understanding, embodiments of the present invention will now be described by way of non-limitative example with reference to the accompanying drawings, in which.

DETAILED DESCRIPTION

Figure 1:
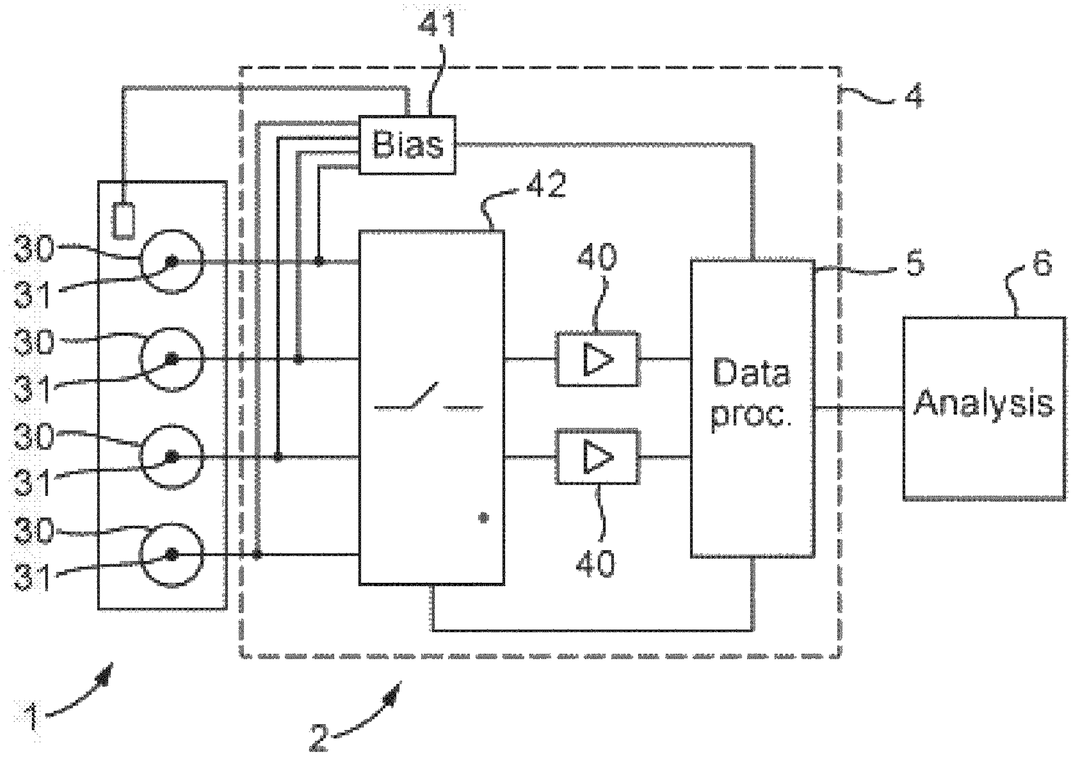
FIG. 1 is diagram of a nanopore array device.

A nanopore array device 1 for sensing interactions of a molecular entities is shown in FIG. 1. The nanopore array device 1 comprises a sensing apparatus 2 comprising a sensor device 3 and a detection circuit 4 that is connected to the sensor device 3.

The sensor device 3 comprises an array of sensing elements 30 that each support respective nanopores that are capable of an interaction with a molecular entity. The sensing elements 30 comprise respective electrodes 31. In use, each sensing elements 30 outputs an electrical measurement at its electrode 31 that is dependent on an interaction of a molecular entity with the nanopore. The sensor device 3 is illustrated schematically in FIG. 1 but may have a variety of configurations, some non-limitative examples being as follows.

Figure 2:
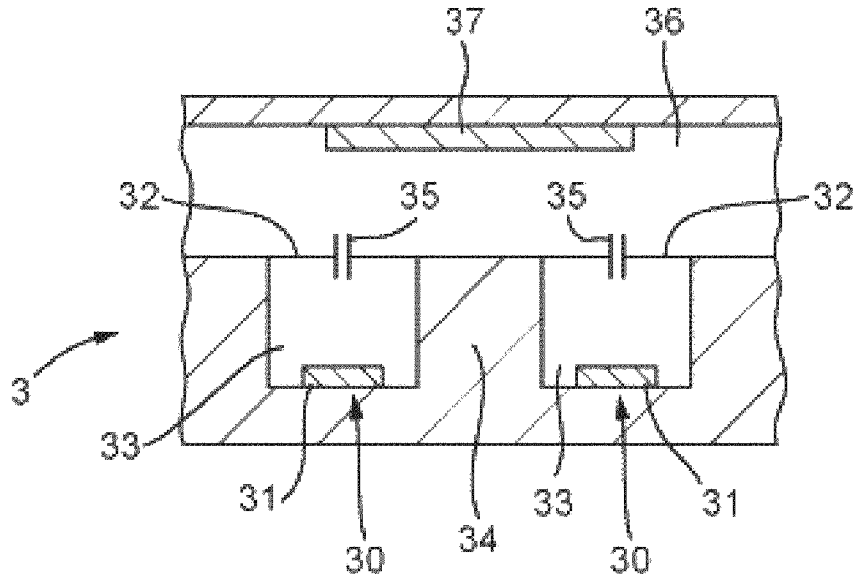
FIG. 2 is a schematic cross-sectional view of part of a nanopore array device.

In one example, the sensor device 3 may have the form shown in FIG. 2. Herein, the sensor device 2 comprises an array of sensing elements 30 which each comprise a membrane 32 supported across a well 33 in a substrate 34 with a nanopore 35 inserted in the membrane 32. The membrane 31 may be made of amphiphilic molecules such as lipid as discussed further below. Each membrane 32 seals the respective well 33 from a sample chamber 36 which extends across the array of sensing elements 30 and is in fluid communication with each nanopore 35. Each well 33 has a sensor electrode 32 arranged therein. A common electrode 37 is provided in the sample chamber 36 for providing a common reference signal (typically a potential or voltage) to each sensor element 30. In use, the sample chamber 36 receives a sample containing molecular entities which interact with the nanopores 35 of the sensing elements 30.

Two sensing elements 30 are shown in FIG. 2 for clarity, but in general any number of sensing elements 30 may be provided. Typically, a large number of sensing elements 30 may be provided to optimise the data collection rate, for example 256, 1024, 4096 or more sensing elements 30.

The sensor device 3 may have a detailed construction as disclosed in WO 2009/077734 or WO 2014/064443 which are herein incorporated by reference in their entireties.

The nanopore and associated elements of the sensing elements 30 may be as follows, without limitation to the example shown in FIG. 2.

The nanopore is a pore, typically having a size of the order of nanometres. In embodiments where the molecular entities are polymers that interact with the nanopore while translocating therethrough in which case the nanopore is of a suitable size to allow the passage of polymers therethrough.

The nanopore may be a protein pore or a solid-state pore. The dimensions of the pore may be such that only one polymer may translocate the pore at a time.

Where the nanopore is a protein pore, it may have the following properties.

The nanopore may be a transmembrane protein pore. Transmembrane protein pores for use in accordance with the invention include, but are not limited to, β-toxins, such as α-hemolysin, anthrax toxin and leukocidins, and outer membrane proteins/porins of bacteria, such as *Mycobacterium smegmatis* porin (Msp), for example MspA, lysenin, outer membrane porin F(OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and a outer membrane proteins, such as WZA and ClyA toxin. The transmembrane pore may be derived from lysenin. The pore may be derived from CsgG, such as disclosed in WO-2016/034591 which is herein incorporated by reference in its entirety. The pore may be a DNA origami pore.

The protein pore may be a naturally occurring pore or may be a mutant pore. The pore may be fully synthetic.

Where the nanopore is a protein pore, it may be inserted into a membrane that is supported in the sensor element 30. Such a membrane may be an amphiphilic layer, for example a lipid bilayer. An amphiphilic layer is a layer formed from amphiphilic molecules, such as phospholipids, which have both hydrophilic and lipophilic properties. The amphiphilic layer may be a monolayer or a bilayer. The amphiphilic layer may be a co-block polymer such as disclosed in WO 2014/064444. Alternatively, a protein pore may be inserted into an aperture provided in a solid-state layer, for example as disclosed in WO 2012/005857.

The nanopore may comprise an aperture formed in a solid-state layer, which may be referred to as a solid-state pore. The aperture may be a well, gap, channel, trench or slit provided in the solid-state layer along or into which analyte may pass. Solid-state layers can be formed from both organic and inorganic materials including, but not limited to, microelectronic materials, insulating materials such as Si3N4, Al2O3, and SiO, organic and inorganic polymers such as polyamide, plastics such as Teflon® or elastomers such as two-component addition-cure silicone rubber, and glasses. The solid-state layer may be formed from graphene.

Molecular entities interact with the nanopores in the sensing elements 30 causing output an electrical signal at the electrode 31 that is dependent on that interaction.

In one type of sensor device 3, the electrical signal may be the ion current flowing through the nanopore. Similarly, electrical properties other than ion current may be measured. Some examples of alternative types of property include without limitation: ionic current, impedance, a tunnelling property, for example tunnelling current (for example as disclosed in Ivanov A P et al., Nano Lett. 2011 Jan. 12; 11 (1): 279-85 which is herein incorporated by reference in its entirety), and a FET (field effect transistor) voltage (for example as disclosed in WO2005/124888 which is herein incorporated by reference in its entirety). One or more optical properties may be used, optionally combined with electrical properties (Soni G V et al., Rev Sci Instrum. 2010 January; 81 (1): 014301 which is herein incorporated by reference in its entirety). The property may be a transmembrane current, such as ion current flow through a nanopore. The ion current may typically be the DC ion current, although in principle an alternative is to use the AC current flow (i.e. the magnitude of the AC current flowing under application of an AC voltage).

The interaction may occur during translocation of the molecular entities with respect to the nanopore, for example through the nanopore.

The electrical signal provides as series of measurements of a property that is associated with an interaction between the molecular entity and the nanopore. Such an interaction may occur at a constricted region of the nanopore. For example in the case that the molecular entity is a polymer comprising a series of polymer units which translocate with respect to the nanopore, the measurements may be of a property that depends on the successive polymer units translocating with respect to the pore.

Ionic solutions may be provided on either side of the nanopore. A sample containing the molecular entities of interest that are polymers may be added to one side of the nanopore, for example in the sample chamber 36 in the sensor device of FIG. 2. membrane and allowed to translocate with respect to the nanopore, for example under a potential difference or chemical gradient. The electrical signal may be derived during the translocation of the polymer with respect to the pore, for example taken during translocation of the polymer through the nanopore. The polymer may partially translocate with respect to the nanopore.

In order to allow measurements to be taken as a polymer translocates through a nanopore, the rate of translocation can be controlled by a binding moiety that binds to the polymer. Typically the binding moiety can move a polymer through the nanopore with or against an applied field. The binding moiety can be a molecular motor using for example, in the case where the binding moiety is an enzyme, enzymatic activity, or as a molecular brake. Where the polymer is a polynucleotide there are a number of methods proposed for controlling the rate of translocation including use of polynucleotide binding enzymes. Suitable enzymes for controlling the rate of translocation of polynucleotides include, but are not limited to, polymerases, helicases, exonucleases, single stranded and double stranded binding proteins, and topoisomerases, such as gyrases. For other polymer types, binding moieties that interact with that polymer type can be used. The binding moiety may be any disclosed in WO-2010/086603, WO-2012/107778, and Lieberman K R et al, J Am Chem Soc. 2010; 132 (50): 17961-72), and for voltage gated schemes (Luan B et al., Phys Rev Lett. 2010; 104 (23): 238103) which are all herein incorporated by reference in their entireties.

The binding moiety can be used in a number of ways to control the polymer motion. The binding moiety can move the polymer through the nanopore with or against the applied field. The binding moiety can be used as a molecular motor using for example, in the case where the binding moiety is an enzyme, enzymatic activity, or as a molecular brake. The translocation of the polymer may be controlled by a molecular ratchet that controls the movement of the polymer through the pore. The molecular ratchet may be a polymer binding protein.

The polynucleotide handling enzyme may be for example one of the types of polynucleotide handling enzyme described in WO 2015/140535 or WO-2010/086603.

Translocation of the polymer through the nanopore may occur, either cis to trans or trans to cis, either with or against an applied potential. The translocation may occur under an applied potential which may control the translocation.

Exonucleases that act progressively or processively on double stranded DNA can be used on the cis side of the pore to feed the remaining single strand through under an applied potential or the trans side under a reverse potential. Likewise, a helicase that unwinds the double stranded DNA can also be used in a similar manner. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential. Alternatively, the single strand DNA dependent polymerases can act as a molecular brake slowing down the movement of a polynucleotide through the pore. Any moieties, techniques or enzymes described in WO-2012/107778 or WO-2012/033524 which are both herein incorporated by reference in their entireties could be used to control polymer motion.

The sensing elements 30 and/or the molecular entities may be adapted to capture molecular entities within a vicinity of the respective nanopores. For example sensing elements 30 may further comprise capture moieties arranged to capture molecular entities within a vicinity of the respective nanopores. The capture moieties may be any of the binding moieties or exonucleases described above with also have the purpose of controlling the translocation or may be separately provided.

The capture moieties may be attached to the nanopores of the sensing elements. At least one capture moiety may be attached to the nanopore of each sensor element.

The capture moiety may be a tag or tether which binds to the molecular entities. In that case the molecular entity may be adapted to achieve that binding.

Such a tag or tether may be attached to the nanopore, for example as disclosed in WO 2018/100370 which is herein incorporated by reference in its entirety, and as further described herein below.

Alternatively in a case the nanopore is inserted in a membrane, such a tag or tether may be attached to the membrane, for example as disclosed in WO 2012/164270 which is herein incorporated by reference in its entirety.

The methods described herein may comprise the use of adapters which adapt the molecular entities for the purpose of capturing them. By way of example, polynucleotide adapters suitable for use in nanopore sequencing of polynucleotides are known in the art. Adapters for use in nanopore sequencing of polynucleotides may comprise at least one single stranded polynucleotide or non-polynucleotide region. For example, Y-adapters for use in nanopore sequencing are known in the art. A Y adapter typically comprises (a) a double stranded region and (b) a single stranded region or a region that is not complementary at the other end. A Y adapter may be described as having an overhang if it comprises a single stranded region. The presence of a non-complementary region in the Y adapter gives the adapter its Y shape since the two strands typically do not hybridise to each other unlike the double stranded portion. The Y adapter may comprise one or more anchors.

The Y adapter preferably comprises a leader sequence which preferentially threads into the pore. The leader sequence typically comprises a polymer. The polymer is preferably negatively charged. The polymer is preferably a polynucleotide, such as DNA or RNA, a modified polynucleotide (such as abasic DNA), PNA, LNA, polyethylene glycol (PEG) or a polypeptide. The leader preferably comprises a polynucleotide and more preferably comprises a single stranded polynucleotide. The adapter may be ligated to a DNA molecule using any method known in the art.

A polynucleotide adapter may comprise a membrane anchor or a transmembrane pore anchor attached to the adapter. For example, a membrane anchor or transmembrane pore anchor may promote localisation of the adapter and coupled polynucleotide within a vicinity of the nanopore. The anchor may be a polypeptide anchor and/or a hydrophobic anchor that can be inserted into the membrane. In one embodiment, the hydrophobic anchor is a lipid, fatty acid, sterol, carbon nanotube, polypeptide, protein or amino acid, for example cholesterol, palmitate or tocopherol.

The anchor may comprise a linker, or 2, 3, 4 or more linkers. Preferred linkers include, but are not limited to, polymers, such as polynucleotides, polyethylene glycols (PEGs), polysaccharides and polypeptides. These linkers may be linear, branched or circular. Suitable linkers are described in WO 2010/086602. Examples of suitable anchors and methods of attaching anchors to adapters are disclosed in WO 2012/164270 and WO 2015/150786 which are both herein incorporated by reference in their entireties.

Examples of tags and tethers which are attached to the nanopore are as follows.

Nanopores for use in the methods described herein may be modified to comprise one or more binding sites for binding to one or more analytes (e.g. molecular entities) and thereby acting as a capture moiety. In some embodiments, the nanopores may be modified to comprise one or more binding sites for binding to an adaptor attached to the analytes. For example, in some embodiments, the nanopores may bind to a leader sequence of the adaptor attached to the analytes. In some embodiments, the nanopores may bind to a single stranded sequence in the adaptor attached to the analytes.

In some embodiments, the nanopores are modified to comprise one or more tags or tethers, each tag or tether comprising a binding site for the analyte. In some embodiments, the nanopores are modified to comprise one tag or tether per nanopore, each tag or tether comprising a binding site for the analyte.

In some embodiments, the tag or tether may comprise or be an oligonucleotide.

Other examples of a tag or tether include, but are not limited to His tags, biotin or streptavidin, antibodies that bind to analytes, aptamers that bind to analytes, analyte binding domains such as DNA binding domains (including, e.g., peptide zippers such as leucine zippers, single-stranded DNA binding proteins (SSB)), and any combinations thereof.

The tag or tether may be attached to the external surface of the nanopore, e.g., on the cis side of a membrane, using any methods known in the art. For example, one or more tags or tethers can be attached to the nanopore via one or more cysteines (cysteine linkage), one or more primary amines such as lysines, one or more non-natural amino acids, one or more histidines (His tags), one or more biotin or streptavidin, one or more antibody-based tags, one or more enzyme modification of an epitope (including, e.g., acetyl transferase), and any combinations thereof. Suitable methods for carrying out such modifications are well-known in the art. Suitable non-natural amino acids include, but are not limited to, 4-azido-L-phenylalanine (Faz) and any one of the amino acids numbered 1-71 in FIG. 1 of Liu C. C. and Schultz P. G., Annu. Rev. Biochem., 2010, 79, 413-444 which is herein incorporated by reference in its entirety.

In some embodiments where one or more tags or tethers are attached to the nanopore via cysteine linkage(s), the one or more cysteines can be introduced to one or more monomers that form the nanopore by substitution.

The transmembrane pore may be modified to enhance capture of polynucleotides. For example, the pore may be modified to increase the positive charges within the entrance to the pore and/or within the barrel of the pore. Such modifications are known in the art. For example, WO 2010/055307 discloses mutations in α-hemolysin that increase positive charge within the barrel of the pore.

Modified MspA, lysenin and CsgG pores comprising mutations that enhance polynucleotide capture are disclosed in WO 2012/107778, WO 2013/153359 and WO 2016/034591, respectively which are all herein incorporated by reference in their entireties. Any of the modified pores disclosed in these publications may be used herein.

The arrangement of the detection circuit 4 will now be discussed. The detection circuit 4 is connected to the electrodes 31 of each sensor element 30 and has the primary function of process the electrical signals output therefrom. The detection circuit 4 also has the function of controlling the application of bias signals to each sensor element 30.

The detection circuit 4 includes plural detection channels 40. Each detection channel 40 receives an electrical signal from a single sensor electrode 31 and is arranged to amplify that electrical signal. The detection channel 40 is therefore designed to amplify very small currents with sufficient resolution to detect the characteristic changes caused by the interaction of interest. The detection channel 40 is also designed with a sufficiently high bandwidth to provide the time resolution needed to detect each such interaction. These constraints require sensitive and therefore expensive components. Each detection channel 40 may be similar to standard single channel recording equipment as describe in Stoddart D et al., Proc Natl Acad Sci, 12; 106 (19): 7702-7, Lieberman K R et al, J Am Chem Soc. 2010; 132 (50): 17961-72, and WO-2000/28312. Alternatively, each detection channel 40 may be arranged as described in detail in WO 2010/122293, WO 2011/067559 or WO 2016/181118.

The analyte of interest to be detected by the nanopore may be a polynucleotide such as DNA or RNA. The analyte may be a polypeptide or a polysaccharide.

The number of sensing elements 30 in the array is greater than the number of detection channels 40 and the nanopore array device is operable to take measurements of a polymer from sensing elements 30 selected in a multiplexed manner, in particular an electrically multiplexed manner. This is achieved by providing a switch arrangement 42 between the sensor electrodes 31 of the sensing elements 30 and the detection channels 40. For clarity, FIG. 1 shows a simplified example with four sensing elements 30 and two detection channels 40, but the number of sensor cells 30 and detection channels 40 is typically much greater. For example, for some applications, the sensor device 2 might comprise a total of 4096 sensing elements 30 and 1024 detection channels 40.

The switch arrangement 42 may be arranged as described in detail in WO 2010/122293. For example, the switch arrangement 42 may comprise plural 1-to-N multiplexers each connected from a detection channel 40 to a group of N sensing elements 30 and may include appropriate hardware such as a latch to select the state of the switching.

By switching of the switch arrangement 42, the nanopore array device 1 may be operated to amplify electrical signals from sensing elements 30 selected in an electrically multiplexed manner. The detection circuit 4 includes a data processor 5 which receives the output signals from the detection channels 40. The data processor 5 acts as a controller that controls the switch arrangement 42 to connect detection channels 40 to respective sensing elements 30 as described further below.

In addition, the detection circuit 4 includes a bias control circuit 41 to perform the function of controlling the application of bias signals to each sensor element 30. The bias control circuit 41 is connected to the common electrode 37 and to the sensor electrodes 31 of each sensor device 30. The bias signals are selected to bias the sensor electrodes 31 with respect to common electrode 37 to control translocation of the molecular entities with respect to the nanopores. In general, it would be possible for a bias signal supplied to a given sensor element 30 to be a drive bias signal that causes translocation to occur at the sensor element 30 or an inhibition bias signal that inhibits translocation to occur at the sensor element 30.

The bias control circuit 41 is controlled by the data processor 5. The data processor has a mode of operation for the bias control circuit 41. Namely, three independent test bias signals are supplied to all the sensing elements 30, thereby causing ionic current flow with respect to the nanopores of each sensing elements 30. The corresponding current flow for each test signal is recorded in the data processor 5 as an amplified electrical signal.

The data processor 5 is arranged as follows. The data processor 5 is connected to the output of the detection channels 40 and is supplied with the amplified electrical signals therefrom. The data processor 5 stores and analyses the amplified electrical signals from the test bias signals to create a calibrated signal. The data processor 5 also controls the other elements of the detection circuit, including control of the bias voltage circuit 41 as described above and control of the switch arrangement 42 as described below. The data processor 5 forms part of the detection circuit 2 and may be provided in a common package therewith, possibly on a common circuit board. The data processor 5 may be implemented in any suitable form, for example as a processor running an appropriate computer program or as an ASIC (application specific integrated circuit).

The data processor 5 of the nanopore array device 1 is connected to an analysis system 6. The data processor 5 also supplies the amplified output signals to the analysis system 6. The analysis system 6 performs further analysis of the amplified electrical signal which is a raw signal representing measurements of the property measured at the nanopore. Such an analysis system 6 may for example estimate the identity of the molecular entity in its entirety or in the case that the molecular entity is a polymer may estimate the identity of the polymer units thereof. Thus, the analysis system may be configured as a computer apparatus running an appropriate program. Such a computer apparatus may be connected to the data processor 5 of the nanopore array device 1 directly or via a network, for example within a cloud-based system.

Figure 3:
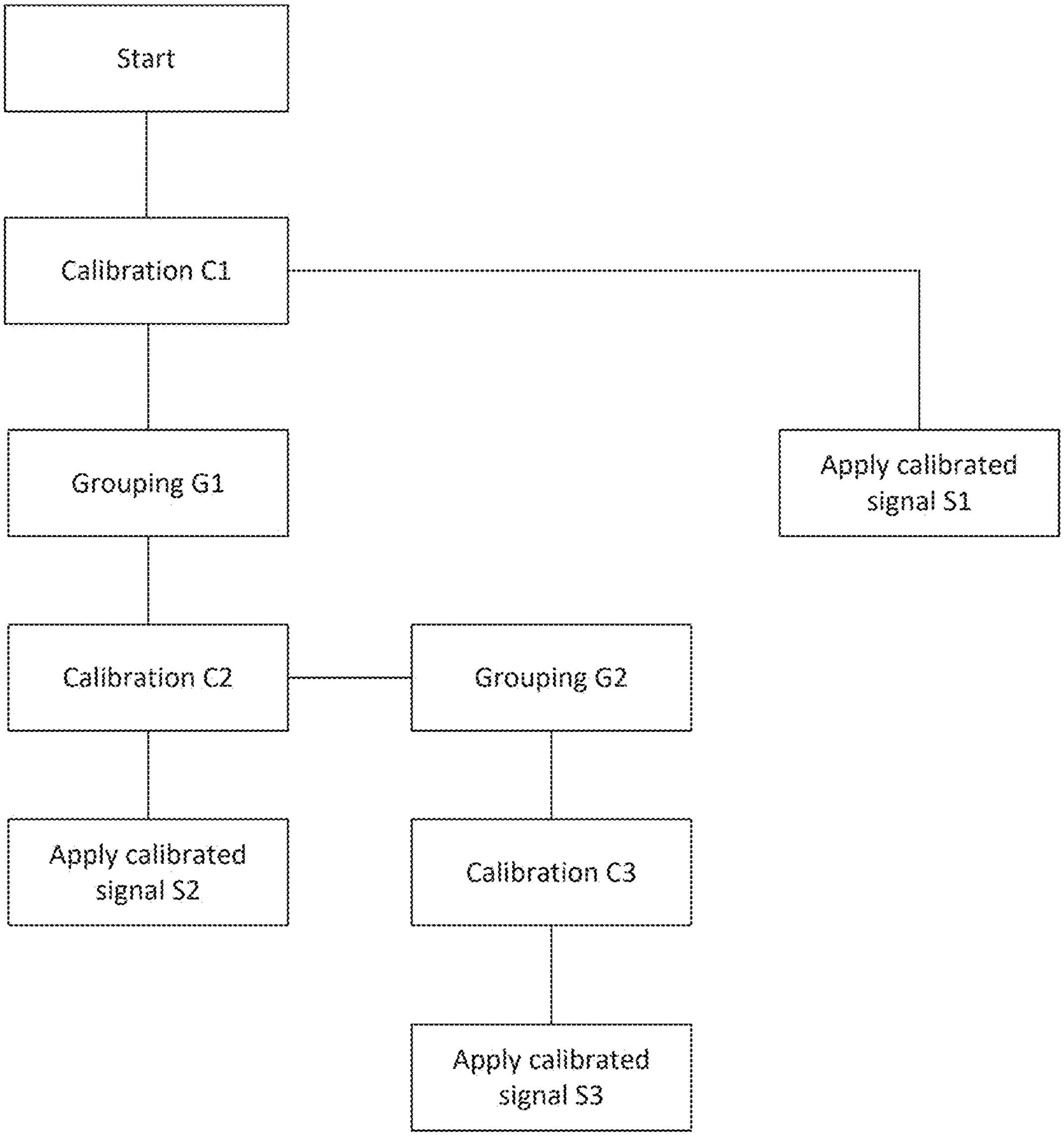
FIG. 3 is a flow chart of a method performed during the calibration of the nanopore array device.

The calibration method of the detection circuit 2 that is performed by the data processor 5 is shown FIG. 3 and performed as follows. The same method is performed in parallel for each detection channel 40.

The method starts with performance of a first calibration C1. For the presently described device, the first calibration is performed by applying three test signals as voltages across the common electrode 37 and the array of sensing electrodes 31. The test signals are smaller in scale than an intended working signal. The test signals are provided typically in the order of magnitude of tens of mV. When applying the test signal it is preferable that the nanopore 35 is free from analyte. In other words, a relatively low test signal is intended so that a meaningful measurement can be taken which is absent of analyte in the nanopore 31 which may interfere with the calibration method.

Figure 4:
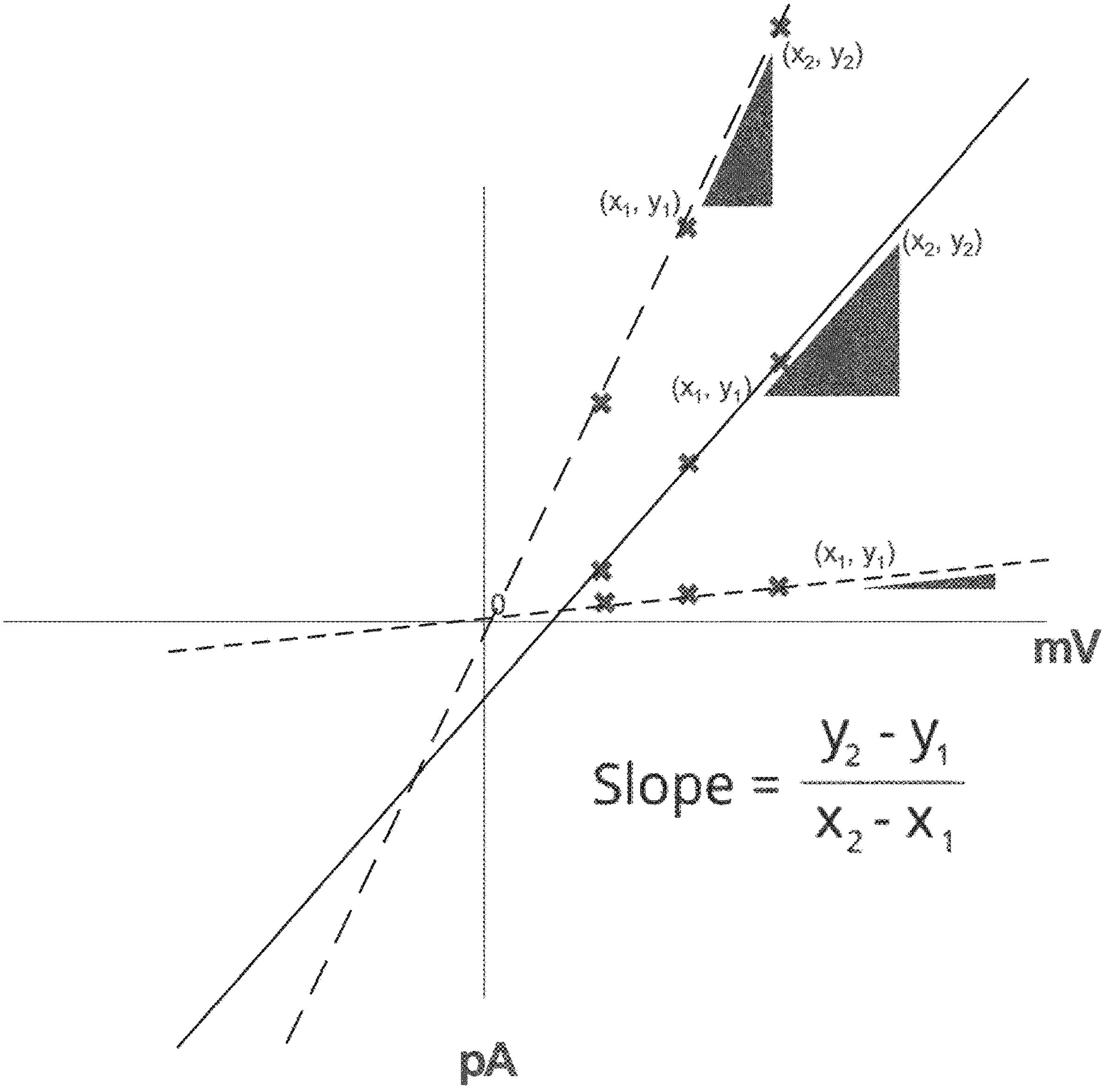
FIG. 4 is a schematic of a logic employed during an embodiment of the calibration method of the present invention.

For each of the sensing electrodes the test voltages will generate a corresponding measured current value. The measured current values are assigned to each sensing electrode 31. These three measured current values are fed into the data processor 5 and plotted on a standard 2D graph, as seen in FIG. 4. The data processor 5 performs a linear regression and for each of the three measure current values for each sensing electrode 31 and determines from the intercept of the linear plot with the y-axis the voltage offset value required for each sensing electrode 31.

In one embodiment, the data processor 5 reviews the offset values for the entire array and determines a global offset value to be applied as a calibration signal S1. The global offset can be determined via statistical analysis of the population of offset values. For example, a mean value could be determined. This mean could be a standard mean, or a weighted mean based on the magnitude of the offset value. Using the standard mean is unfavourable since any skew in the data or outlying offset value will have little influence on the calculated global offset value. In addition it would be complex to attribute correct weighting to offset values to record a true weighted mean for each calibration. Alternatively the mode offset value could be selected as the global offset value. However, this is unfavourable since there may be two or more modes in the offset value data. In another alternative the median offset value could be assigned as the global offset value. This is more most favourable because the median offset value is unaffected by any extreme outliers or non-symmetric distributions of offset values.

This simplistic embodiment does not take into account the quality or potential performance of any of the sensing elements 30. An alternative additional step may be performed at this stage by the data processor 5 referred to as grouping G1 in FIG. 3. An example of grouping might be based on an additional analysis of the linear regression performed to provide the offset values for each sensing electrode 31. The data processor might review the gradient of each of the linear plots corresponding to the test signals and measurements from each sensing electrode 31. The gradient may give a quick assessment of the performance of the sensing elements 31. The data processor 5 can simply discount sensing elements 30 with too high or low gradient values (as seen as the dashed line plots in FIG. 4). In addition, the data processor 5 may also profile and then collate sensing elements 30 into any number of groups based on their performance. For example, some of these groups may be labelled as functional and operational sensing elements 30, other may be labelled as defunct sensing elements 30, other may be labelled as reserved sensing elements 30 that could be replenished or recharged.

In a more detailed example, the data processor 5 may additionally analyse the test signals and measurements to detect sensing elements 30 which do not have an acceptable quality of performance because it is not that case that a membrane has formed and an acceptable number of membrane proteins have inserted and record the results. In that case, the data processor 5 may avoid selecting sensing elements 30 where this is the case, thereby effectively apply techniques similar to those disclosed in WO 2010/122293 but in combination with the additional steps disclosed herein.

An alternative example of grouping will now be described. The data processor 5 may select new sensing elements 30 for connection to the respective detection channels 4 in any suitable manner, taking account of the connections that the switch arrangement 42 is capable of making. For example in the case that the switch arrangement 42 comprises plural 1-to-N multiplexers, the data processor 5 may select sensing elements 30 of each group of N sensing elements 30 successively in a regular cycle for connection to the corresponding detection channel 40.

Either of these two grouping methods can be applied at stage G1. In any event, for each group a new cycle of calibration C2 is performed as per the method of the present invention to generate a calibrated signal S2. For the first grouping method, the data processor 5 can determine a calibrated signal S2 for each group as necessary. Then during use of the nanopore array device 1 the appropriate calibrated signal S2 per group can be employed. The statistical analysis to generate the calibration signal S2 is the same as that employed to generate S1.

For the second grouping method a calibrated signal S2 is generated for each group of N sensing elements 30. Similarly, the statistical analysis to generate the calibration signal S2 is the same as that employed to generate S1.

If the second grouping method is employed, an optional additional grouping may be carried out G2 similar to the first grouping method of G1. Namely, for each group of N sensing elements 30, the gradient from the plot corresponding to the test signals of each sensing electrode 31 is reviewed by the data processor to remove plots with gradients with too high or low values. In any event, for each group a new cycle of calibration C3 is performed as per the method of the present invention to generate a calibrated signal S3. Similarly, the statistical analysis to generate the calibration signal S2 and S1 is the same as that employed to generate S3.

The calibrated signals S2 and S3 can have additional step of generating a global offset value which can be applied for each of the sensing electrode 31 across the array. This global offset value is applied The calibration or profiling method of the present invention can be employed prior to the initial use of the nanopore array device 1. Additionally or alternatively, the calibration or profiling method of the present invention can be used once the nanopore array device 1 has been used to sense or detect an analyte of interest.

The invention claimed is:

1. A method of calibrating a nanopore array device, the nanopore array device comprising: a common electrode, an array of sensing elements each comprising a sensing electrode and a nanopore channel, and an ionic solution in contact with the common electrode and the array of sensing electrodes, the ionic solution providing electrical communication between the common electrode and each of the array of sensing electrodes via the corresponding array of nanopore channels;

the method comprising:

applying a two or more test signals across the nanopore channels between the common electrode and array of sensing electrodes;

measuring a corresponding current or voltage value associated with each sensing electrode for each test signal, determining an offset value for each sensing electrode from the measured current or voltage signals, and calculating a general offset value from the determined offset values, and applying a calibrated signal between the common electrode and sensing electrodes; wherein the calibrated signal is adjusted by the general offset value.

2. The method according to claim 1, wherein the calibrated signal is a voltage, the test signals are voltages, and the offset value is a voltage such that the corresponding measurements associated with each test signal is a measurement of current.

3. The method according to claim 1; wherein the sensing electrodes are divided into groups, and a general offset value is determined for each of the groups of sensing electrodes.

4. The method according to claim 1, wherein a global offset value is determined across the entire array of sensing electrode.

5. The method according to claim 1, wherein the method includes an additional step of carrying out a linear regression to determine the offset value.

6. The method according to claim 5, wherein the method includes estimating a gradient value from the linear regression.

7. The method according to claim 1, wherein at least three test signals are applied across the common electrode to give three or more corresponding current or voltage measurements associated with each test signal.

8. A method according to claim 1, wherein the nanopore array device further comprises a redox mediator, and the sensing electrodes and common electrode are selected from an inert metal.

9. The method according to claim 1, wherein each sensing element in the array comprises a well which houses a corresponding sensing electrode, and each nanopore channel comprises a protein pore inserted in an amphiphilic membrane, the amphiphilic membrane extending across an opening of each of the wells.

10. The method according to claim 1, wherein the nanopore channel comprises a nanopore provided in a solid-state substrate.

11. The method according to claim 2, further comprising the step of measuring ion current through a nanopore under the application of the calibrated voltage.

12. The method according to claim 11, wherein the ion current is measured to determine the interaction of an analyte of interest with a nanopore.

13. The method according to claim 12, where the analyte of interest is a polynucleotide and the measured ion current is due to translocation of the polynucleotide through a nanopore.

14. The method according to claim 1, wherein the method is performed after the calibrated signal has been used for one or more successive periods of time, such that new offset values, a new general offset value and a new calibrated signal are calculated for each period of time.

15. The method according to claim 14, wherein a sensing electrode having an offset value falling outside of a threshold value is disconnected from the nanopore array device.

16. The method according to claim 15, wherein a sensing electrode is reconnected after a further period of time where it is determined that the new offset value for said sensing electrode falls within a new threshold value.

17. The method according to claim 15, wherein the offset value for a sensing electrode whose offset value is determined as being greater than the new threshold value is not used to calculate the general offset value.

18. The method according to claim 1, wherein the offset value for a sensing electrode whose offset value is determined as being greater than a threshold value is not used to calculate the general offset value.

19. The method according to claim 1, wherein the test signals are applied below a limit value relative to the calibrated signal.

* * * * *